United States Patent [19]

Hurwitz et al.

[11] Patent Number: 4,645,748

[45] Date of Patent: Feb. 24, 1987

[54] PROTEIN WHICH IS CHARACTERISTIC OF RHEUMATOID ARTHRITIS

[76] Inventors: Charles Hurwitz, 108 Mosher Rd., Delmar, N.Y. 12054; Carmen L. Rosano, 23 Nancy Dr., Troy, N.Y. 12180; Nourollah Parhami, 349 Torquay Blvd., Westmere, N.Y. 12203; Karim Hechemy, 29 Pico Rd., Clifton Park, N.Y. 12065

[21] Appl. No.: 697,332

[22] Filed: Feb. 1, 1985

[51] Int. Cl.[4] ............... G01N 33/53; G01N 33/563; G01N 33/564
[52] U.S. Cl. .................................. 436/509; 436/512; 436/513; 436/547; 436/808; 436/821; 530/380; 530/388; 530/417; 530/419
[58] Field of Search ............ 260/112 R, 112 B; 436/509, 512, 808, 821, 513, 547; 530/380, 388, 417, 419

[56] References Cited

U.S. PATENT DOCUMENTS 4,499,186   2/1985   Teodorescu ............... 436/509 X

OTHER PUBLICATIONS

Rosano, C. L. et al., Biochem. Biophys. Res. Commun., 128(3), 1288–1294, (1985).
Chemical Abstracts, 101:5047j, (1984).
Tellerova, K. et al., J. Chromatog., 273(1), 197–201, (1983).
"Plasmapheresis", Nose, Y. et al., eds, pp. 37–43 by Kanamono, T. et al., ISAO Press, Cleveland, 1983.

*Primary Examiner*—Sidney Marantz
*Attorney, Agent, or Firm*—Wyatt, Gerber, Shoup, Scobey and Badie

[57] ABSTRACT

Describes rheumatoid arthritis factor present in detectable amounts in rheumatoid arthritis patients, but not in patients with other arthritedes; preparation of antibodies to the factor; use of factor and antibodies to test for rheumatoid arthritis; and test kits for conducting the tests.

8 Claims, No Drawings

PROTEIN WHICH IS CHARACTERISTIC OF RHEUMATOID ARTHRITIS

BACKGROUND OF INVENTION

Rheumatoid arthritis (RA) has been described as an unresolved systemic inflammation in which immune dysfunction and genetic susceptibility play roles. In earlier stages it is characterized by fluctuating remissions and exacerbations, and in later stages by a chronic granulatomous response (panus formation) leading to tissue destruction. The synovial membrane in RA has many of the characteristics of a hyperactive immunologically stimulated lymphoid organ and the ratio of T suppressor to T helper lymphocytes has been shown to be significantly reduced.

Although a number of attempts have been made to implicate bacteria, viruses and mycoplasms as etiological agents, no specific causative agent has been clearly proven. It is possible that there is no specific etiological agent, and that the important agent or factor may be the result of an interplay of hereditary factors and physiological changes on non-specific inflammatory states.

A great deal of work has been expended on the late, destructive phase of this disease in which anaphylactically induced leukotrienes and prostaglandins may play a chemotactic role in migration of neutrophils and macrophages into the rheumatoid synovium leading to destruction of bone and cartilage. Many attempts have been made to intervene between these events and the subsequent destructive phase occurring in the rheumatoid synovia.

Since there is no unambiguous test distinguishing RA from other acute or chronic inflammatory diseases, differentiating RA from other arthritides, such as systemic lupus erythematosus, (SLE) ankylosing spondylitis, (AS), polyarticular gout (PAG), psoriatic arthritis (PsA), etc., is often difficult. Diagnosis of RA is usually made according to American Rheumatism Association (ARA) criteria. As seen from Table 1, a patient whose symptoms meet at least 3 of the 8 criteria is considered probably to have RA, while a definite clinical diagnosis is usually not made until 5 or more of the symptoms are positive. However, it is not unusual for diagnoses to be changed after further observations, since complications in diagnosis may result from overlapping symptoms, and the presence of symptoms from one arthritides does not preclude the possibility that the patient may also have another arthritic disease.

TABLE 1

1. MORNING STIFFNESS
2. JOINT TENDERNESS OR PAIN ON MOTION
3. SOFT-TISSUE SWELLING OF THE JOINT
4. SOFT-TISSUE SWELLING OF A SECOND JOINT (Within 3 months)
5. SOFT-TISSUE SWELLING OF SYMMETRICAL JOINTS (Excludes distal interphalangeal joint)
6. SUBCUTANEOUS MODULES
7. X-RAY CHANGES
8. SERUM POSITIVE FOR RHEUMATOID FACTORS PROBABLE RA=3 or 4 POINTS
DEFINITE RA=5 or more points A specific objective measurement which could provide an unambiguous diagnosis of RA would be an enormous aid to the rheumatologist. Such a test would be even more important if it could be used to assess the response to therapy and to predict activation and reactivation of the disease process. Such a test might enable its prevention by early institution of therapy.

One test is presently available. It is based upon an antibody (rheumatoid factor) to the Fc fraction of IgG. Rheumatiod Factor (RF) is present in about 60% to 70% of those individuals afflicted with RA. The test is not satisfactory because it has been found to give unacceptably large numbers of false positives or negatives, and it does not assess the response to therapy or predict activation or reactivation of the disease process.

THE INVENTION

It has now been discovered that there is a rheumatoid arthritis protein (RHP) characteristically present in detectable amounts in the sera of RA patients but is not detectable in sera from normal individuals or in sera from patients with other arthritides. This protein is not RF nor any of the known acute phase reactants. RHP can be isolated and used to prepare polyclonal and monoclonal antibodies which can be used to detect RA and to follow the course of treatment of the disease. These antibodies can be provided in test kits which can be used to serodiagnose clinically suspected RA patients in various clinical settings including the doctor's office.

This protein can be recognized and distinguished from other proteins by the following characteristic properties:

1. Isolectric pH range of 5.1 to 5.3.
2. Precipitated from human serum in 0.02 molar acetate buffer at pH 5.5 (the euglobulin fraction).
3. Soluble in 0.026 molar ethylene glycol tetraacetic acid (EGTA) at pH 7.5.
4. Present in euglobulin fraction of human sera.
5. Molecular weight of about 135,000 as detected by sodium dodecyl sulfate polyacrylamide gel electrophoresis (SDS-PAGE).
6. Enlarges the size of the Clq precipitin ring in radial immunodiffusion (RID).
7. Inhibits the hemolytic activity of Clq.
8. Inhibits the binding of Clq to fibronectin.
9. Over 90% by weight of the total molecular weight is accounted for by the following amino acids.

| | |
|---|---|
| Aspartic acid, ASP | Alanine, ALA |
| Threonine, THR | Valine, VAL |
| Serine, SER | Phenylalanine, PHE |
| Glutamic acid, GLU | [1]Histidine, HIS |
| Proline, PRO | Glycine, GLY |
| Isoleucine, ISOLEU | Cysteine, CYS |
| Leucine, LEU | |
| Tyrosine, TYR | |
| Lysine, LYS | |
| Arginine, ARG | |

10. Nonreactive with antibodies to human IgG, IgA and IgM.

The following sections of this application will include:

1. A materials and methods section to describe generally the procedures used to isolate, detect, test and characterize RHP.
2. An isolation and purification section to describe how RHP is obtained from human sera and purified.
3. A characterizing section to describe how the characterizing properties of RHP were determined.

4. A differentiating section to describe how RHP differs from other materials including those often said to be characteristically present in RA.

5. An antibody section to describe the preparation of polyclonal and monoclonal antibodies to RHP.

6. An RA detecting section to describe how the antibodies to RHP can be used to detect RA.

7. A test kit section to describe test kits containing RHP, and methods of using the kits.

1. MATERIALS AND METHODS SECTION

Measurement of Clq

Clq was measured at diffusion equilibrium by the single radial immunodiffusion method of Mancini et al Int. J. Immunochem. 2: 235,1965, using purified agarose (Biorad, zero-$m_r$). The anti Clq (goat, 7% solution) was obtained from Atlantic Antibodies, Scarborough, Me., and was used at a dilution of 1:250. Clq was also measured by the hydroxyproline method of Rosano et al: J. Lab. Clin. Med. 94: 593,1979, Clin. Chem. 23: 1335, 1977. The latter method consists of calculating the Clq content of serum from the hydroxyproline content of the euglobulin fraction which contains all the Clq and no other hydroxyproline-containing protein.

Purification of Clq and fractionation of serum

Clq was purified by the procedure of Yonemasu and Stroud J. Immunol. 106: 304, 1971, yielding 5 serum fractions: (a) the noneuglobulin fraction, (b) the 0.026M EGTA eluate of the euglobulin fraction (S1), (c) the 0.06M EGTA eluate (S2), (d) the 0.035M EDTA eulate (S3), and (e) the purified Clq which contains less than 3% impurities present as immunoglobulins (2). The procedure and yields are outlined in Table 2. RHP was isolated from the S1 fraction.

TABLE 2

PURIFICATION OF ClQ
1 ml of serum dialysed vs. saline

+8 ml of 0.02 M acetate buffer, pH 5.5

[a] Supernatant(noneuglobulin)   Precipitate(euglobulin)
  58 mg protein                   2.30 mg protein Dialysis vs 0.026 M EGTA-pH 7.5

[b] Eluate (S1)                   Precipitate
  1.47 mg protein                 0.864 mg protein Dialysis vs. 0.06 M EDTA-pH 5.0

[c] Eluate (S2)                   Precipitate
  0.521 mg protein                0.314 mg protein Dialysis vs. 0.035 M EDTA-pH 7.5

[d] Eluate (S3)                   [e] Precipitate (Clq)
  0.270 mg protein                0.053 mg protein Preparation of Clq-depleted serum Serum lacking Clq was prepared by the procedure of Kolb et al: J. Immunol. 122: 2103, 1979. This procedure consists of passing serum through a column of Sepharose 4B covalently bonded to IgG which removes all Clq without affecting the other hemolytic complement components of serum.

Electrofocusing

Electrofocusing was performed using the flat-bed LKB Multiphor unit (LKB, Washington, D.C.). The gel consisted of 5% washed Sephadex G-75 (Superfine, Pharmacia, Piscataway, N.J.) into which was incorporated 5% ampholytes (Bio-Lyte, BioRad, Richmond, Calif.), and from 2 to 7 mg of protein from S1 fractions. The proteins were resolved by exposure to 7 watts for 18 hours. The gel bands containing the resolved proteins were suspended in distilled water for determination of pH, and eluted with 10 ml of 0.1M phosphate buffer, pH 8.0, followed by 10 ml of water. Ampholytes were removed by dialysis vs normal saline.

Preparative electrofocusing was also performed with a Model 8101 apparatus (LKB Instruments, Inc., Hicksville, N.Y. 11801), using a 0–50% glycerol gradient containing Brij 35 and ampholytes, pH 4–7. The gradient was charged with 55 mg of protein solution, and electrofocusing was accomplished by exposure to about 2W for 72 hours. At equilibrium the voltage was 800 v and the amperage was 2.5 mA. The gradient was collected in 3.5 ml aliquots by gravity flow.

Column chromatography

A DEAE-cellulose column (6.5×0.8 cm, DE 52, Whatman, Clifton, N.J.) was equilibrated with 0.047M phosphate buffer, pH 7.5 containing 0.002M EDTA. The column was charged with protein and eluted with the indicated NaCl gradients.

HPLC gel-filtration

A biorad TSK 250 column was charged with protein isolated by DE 52 chromatography and was eluted with 0.1 molar sodium sulfate plus 0.02 molar sodium phosphate buffer (pH 6.8) at 250 psi to give a flow rate of 1 ml per minute.

Sodium dodecyl sulfate polyacrylamide gel electrophoresis (SDS PAGE)

Eectrophoresis was performed by the slab gel technique descrioed by Laemmli: Nature 227: 680, 1970.

Protein determinations

The methods for protein determination have been described by Lowry et al: J. Biol. Chem. 193: 265, 1951, and M. Bradford: Anal. Biochem. 72: 248, 1976.

Patients

All RA patients met 5 or more of the ARA criteria. Their disease was active, of 2–10 years duration, and partially suppressed by non-steroidal anti-inflammatory drugs. Patients with SLE, AS and PsA also had active disease being treated with non-steroidal anti-inflammatory drugs. Patients with gout had active disease and had received no treatment before blood samples were drawn. Patients with AS had no peripheral joint involvement.

2. ISOLATION AND PURIFICATION SECTION

To 10 ml of dialyzed serum (vs. saline) was added 80 ml of 0.02M acetate buffer pH 5.5. It was allowed to stand overnight at 5° C. then centrifuged for 30 minutes at 5,000 rpm.

The supernate was discarded and the precipitate dissolved in 5 ml of 0.5M NaCl. The dissolved precipitate (euglobulin) was dialyzed vs. 1 liter of 0.026M EGTA pH 7.5 (two changes over 20 hrs.)

The solution was centrifuged and the precipitate was discarded. The supernatant contained approximately 11 mg of protein (S1 fraction).

This is the S1 fraction from Table 2. Since, as will be shown below, RHP is present in the S1 fraction it is apparent that RHP is:

1. Precipitated from human serum in 0.02 molar acetate buffer at pH 5.5.

2. Soluble in 0.026 molar EGTA at pH 7.5.

The S1 fraction was dialyzed vs. 0.04M Tris pH 7.5+0.05M NaCl. The approximately 5 ml of S1 fraction was put on a (40×0.9 cm) DE 52 column previously equilibrated with the same (Dialysis) buffer. Proteins were eluted with 0.04M Tris pH 7.5 containing a gradient of 0.05 molar to 0.15 molar sodium chloride. Collecting 3 ml fractions, RHP appeared after tube 22, and was completely off the column after tube 31. This protein peak contained approximately 600 µg protein and was further purified by dialysis against 0.1M $Na_2SO_4$+0.02M $NaH_2PO_4$—$Na_2HPO_4$ buffer, pH 6.8.

The RHP protein mixture was further purified by HPLC column chromatography using a TSK-250 column. The proteins were eluted with 0.1M $Na_2SO_4$+0.02M $Na_2HPO_4$—$Na_2HPO_4$ buffer pH 6.8. The RHP protein was eluted after 7.4 minutes at 1 ml/min, 300 psi.

This protein was further purified using an HPLC column (DEAE-5PW) with a step-wise increase in salt concentration to elute protein. Equilibrating buffer was 0.04M Tris pH 7.5 and the salt (NaCl) additions to this buffer were 0.05M, 0.10M, 0.3M. The RHP was eluted after the second step (0.1M NaCl) and the amount of protein recovered was approximately 100 µg. The protein obtained from this peak was resolved by SDS PAGE and appeared to be pure by silver stain.

Another isolation procedure is based upon the observation that the Clq precipitin ring was observed to be enlarged when the sera of RA patients was tested. Clq is a complement fraction. It has been shown by Rosano et al: J. Lab. Clin. Med. 103:313, 1984 that Clq in the sera of non-RA patients, or in the euglobulin fraction of their sera can be correctly estimated by RID if standard curves are prepared from Clq depleted serum. However, assays of Clq content of RA sera or the euglobulin fraction of RA sera were consistently overestimated by this procedure. The reason for this overestimation is the presence of RHP in the euglobulin fraction or the S1 fraction of RA sera.

To establish the presence of RHP in S1 , the S1 fraction from the sera of RA patients was electrofocused in ampholyte-Sephadex G-75, pH 4 to 8. This resolved the proteins into about 15 detectable bands, each of which was scooped out and its pH determined.

The proteins in each band were then tested for ability to increase the size of the precipitin ring. Each well contained 0.5 µg of isolated protein and 0.75 µg Clq. The only band which caused an increase in the size of the precipitin ring was the band in the isoelectric pH range, 5.1 to 5.3.

This study established a procedure to isolate RHP and established that RHP:

1. Is present in the euglobulin fraction of human sera.
2. Has an isoelectric pH range of 5.1 to 5.3.

Any of the isolated fractions described in this Isolation and Purification section can be used to produce anti-RHP antibodies. This includes the S1 fraction itself and, for example, the first fraction purified by HPLC.

3. CHARACTERIZING SECTION

Determination of molecular weight

The proteins in the pH 5.1–5.3 band of the S1 fraction were subjected to SDS·PAGE against the following known standards:
  myosin—200,000 Daltons
  phosphorylase B—92,500 Daltons
  β-galactosidase—116,000 Daltons
  bovine serum albumim—66,000 Daltons
  ovalbumin—45,000 Daltons Eight bands ranging in molecular weight from about 28,600 to 180,000 were separated. Most of the protein of this fraction was found in two bands, having molecular weights of 76,000 and 135,000 Dalton. The latter manifests the most activity in enlarging the precipitin ring. RHP is non-reactive with antibodies to IgG, IgA and IgM In this test, 0.1 ml of an RA S1 fraction containing 110 µg protein was exposed to 20 mg of immunobead reagent (immunobead Rabbit antihuman immunoglobulins G, A and M, heavy and light chains, Bio Rad Laboratories). The beads are therefore capable of removing these immunoglobulins from sera or other materials containing them. The specific beads employed in this test were separately determined to be capable of removing 10 µg IgA, 139 µg IgG and 61 µg IgM. The 0.1 ml of S1 used in the test contained less than these amounts of the three immunoglobulins. When the test was completed no immunoglobulins were detectable in the treated S1 fraction and yet it was still capable of enlarging the Clq precipitin ring. It should be noted that RF is an immunoglobulin, usually IgM.

RHP inhibits the hemolytic activity of Clq

A known requirement for the hemolytic activity of Clq is the binding of Clr-Cls complement component to form Cl. It has been observed (Rosano et al: J. Lab. Clin. Med. 103: 313,1984) that elevated serum levels of Clq in active cases of RA are not accompanied by increased levels of Clr and Cls. The effect of RHP on the hemolytic activity of Clq was examined by a modification of the procedure of Kolb et al, cited above. In this procedure up to 1.6 µg of RHP was added to 0.25 µg of purified Clq in 30 µl of a 1:1 dilution of Clq-depleted serum and 0.2 ml of a 1:5 dilution of activated red blood cells in veronal buffer, pH 7.3 containing 0.1% of bovine serum albumin. Hemolysis was measured as the increase in absorption at 412 nm after 25 minutes at 37° C. It was observed that 1.6 µg of RHP completely inhibited the hemolytic activity of 0.25 Ng. of Clq in the presence of the Clr-Cls contained in 30 µl of Clq depleted serum. Thus RHP prevented the hemolytic activity of Clq even in the presence of excess amounts of Clr-Cls.

RHP inhibits the binding of Clq to firbronectin

It is known that fibronectin binds to Clq with a $K_D$ of 82 nM, and that the binding takes place in the hinge region of the collagen-like and globular domains of Clq. See Bing et al: Proc. Natl. Acad. Sci. USA 79: 4198, 1982 and Reid et al: Actu. Path. Micrbiol. Immunol. Scand. Sec. C Suppl. 248, Vol. 92:11, 1984. The procedure of Bing et al was utilized to establish that RHP inhibits the binding of Clq to fibronectin.

In this procedure, 5 µg of fibronectin in 1 ml PBS (0.01M sodium phosphate, pH 7.4 in 0.15M NaCl) was adsorbed to 12×75 mm polystyrene tubes at 4° C. and the excess removed by aspiration. 40 ng of $125_{I-Clq}$ was added to each tube. Tube 1 contained Clq but no fibronectin; tube 2 contained fibronectin plus Clq and tube 3 contained Clq, fibronectin and 340 ng of RHP. The tubes were incubated for 30 minutes at 32° C., washed three times by aspiration with PBS and the residual radioactivity measured with a gamma counter (Ortec well). The results are summarized in Table 3.

TABLE 3

| Effect of RHP on binding of $^{125}I$—Clq to fibronectin | |
|---|---|
| | Counts per minute |
| (1) No fibronectin | 2 ± 1 |
| (2) + fibronectin | 108 ± 2 |
| (3) + fibronectin + RHP | 60 ± 2 |

For this study RHP was purified by electrofocusing the S1 fraction from RA serum, followed by SDS-PAGE. The 135,000 Dalton band from the electrophoresis was extracted as the source of RHP.

It will be observed from the results reported in the table that the amount of fibronectin bound $125_I$-Clq was reduced by 44% in the presence of the added RHP.

Amino acid analysis of RHP

A purified sample of RHP was analyzed for its amino acid content. Analysis was conducted with a Durrum D-500 Amino Acid Analyzer using 19 ug samples which were hydrolyzed with 6N HCl. The total amino acids in Table 4 account for over 90% of the molecular weight as determined by SDS-PAGE. RHP contains no detectable hydroxyproline.

TABLE 4

| Amino Acid Content of RHP | | |
|---|---|---|
| AA's | ug | % |
| Glu | 2.63 | 15.1 |
| Asp | 2.22 | 12.8 |
| Tyr | 1.54 | 8.9 |
| Gly | 1.45 | 8.3 |
| Pro | 1.32 | 7.6 |
| Ser | 1.20 | 6.9 |
| Arg | 1.18 | 6.8 |
| Lys | 1.10 | 6.3 |
| Val | 0.76 | 4.4 |
| Phe | 0.73 | 4.2 |
| Thr | 0.64 | 3.7 |
| Leu | 0.62 | 3.6 |
| His | 0.61 | 3.5 |
| Ala | 0.58 | 3.3 |
| Isoleu | 0.57 | 3.3 |
| Cys | 0.25 | 1.4 |

4. DIFFERENTIATING SECTION

The studies reported above and other studies make it clear that RHP is not identical with a number of factors which have been associated with RA or the Clq degradation products.

The amino acid analysis which accounts for over 90% of the molecular weight of RHP eliminates the possibility that RHP is the chondroictin-4- sulfate proteoglycan Clq inhibitor reported by Silvestri et al: J. Biol. Chem. 256: 7383, 1981, since the latter contains only 9% protein. Additionally, (1) serine, glycine and glutamic acid constitute 50% of the total amino acids of the proteoglycan inhibitor but less than 20% of RHP; (2) at 0.15M NaCl, the proteoglycan inhibitor decreases the size of the Clq-anti Clq precipitin ring, while RHP increases its size.

RHP is not one of the acute phase reactants commonly observed in the sera of patients with inflammatory diseases. To establish this fact, RHP purified by HPLC as described above was tested for identity with orosomucoid, haptoglobin, alpha antitrypsin, and $C_3$ by immunoelectrophoresis against their respective monospecific antisera. In these tests a pool of normal phase RA human serum was diluted 1:3 to achieve concentrations of acute phase reactants comparable to the concentration of RHP being tested. In each instance, the monospecific antiserum gave a distinct line with its acute phase protein, but in no case did these antisera produce a reaction with purified RHP.

RHP is not the rheumatoid factor or an immunoglobulin since the enhancing effect of the S1 fraction of an RA serum is not decreased by the total removal of IgA, IgG and IgM.

The fact that RHP contains no demonstrable hydroxyproline makes it clear that it is not a subunit of Clq or a subunit aggregate of Clq containing its collagen like domain.

5. ANTIBODY SECTION

Polyvalent rabbit anti-RHP serum was prepared by intramuscular injection of purified RHP in Freund's complete adjuvant, followed by a booster injection after 7 days. The rabbit was bled from the ear on days 7 and 20 and the total immunoglobulin from the serum was obtained by $(NH_4)_2SO_4$ fractionation. The rabbit anti-RHP titers were determined by hemagglutination of tanned sheep red blood cells sensitized with purified RHP. The titer after 7 days was 1280 and increased to at least 20,480 after twenty days.

There follows a description of the specific procedures utilized to: (1) prepare polyvalent antibody to RHP in rabbits; (2) detect the presence of antibody to RHP in rabbit serum and (3) separate antibody to RHP from rabbit serum.

PRODUCTION OF ANTIBODY IN RABBIT TO RHP

1. Rabbits 2 to 3 kg, are used for the production of antibody to RHP.
2. Five ml of blood is collected one day before inoculation. The blood is allowed to clot, and the serum is separated from the clot by centrifuging decanting to separate the serum control.
3. Next day, 100 μg of RHP in 0.2 to 0.4 ml of saline is thoroughly mixed with an equal volume of Freund's complete adjuvant.
4. The suspension is then administered intramuscularly into the rabbit.
5. Seven days after the first injection 5 ml of blood is drawn and the serum obtained as described above.
6. Next day, 60 to 100 μg of RHP in 0.2 to 0.4 ml of saline is thoroughly mixed with an equal volume of Freund's adjuvant.
7. The suspension is then administered to the rabbit intramuscularly.
8. Seven days after the second injection, 10 to 20 ml of blood is collected and procesed as described above.
9. Blood is collected if needed at 2-week intervals.

DETECTION OF ANTIBODY TO RHP IN RABBIT SERUM

1. A hemagglutination assay was performed to determine the antibody titer to RHP.
2. Sheep red blood cells (RBC) are standardized to 3%.
3. To this standardized 3% RBC suspension, an equal volume of 1:20,000 tannic acid solution is added. The mixture is mixed by inverting the tube and incubated at 37° C. for 15 minutes. Invert the tube at 5-minutes interval to keep the RBC in suspension.
4. Centrifuge at 2,000 rpm for 12 minutes. Discard supernate. Add 10 ml of PBS pH 7.2 to the RBC pellet and mix.
5. Centrifuge at 2,000 rpm for 12 minutes and discard supernate. Add 5 ml of PBS pH 6.4. Resuspend thoroughly. Adjust volume of suspension with PBS pH 6.4 so that the concentration of the tanned RBC is 3%.
6. The suspension is divided into 2 equal portions. One portion is labeled RHP sensitized and the other portion is labeled bovine albumin, fatty acid free (BAF) sensitized. The latter suspension acts as control in the serologic reaction.
7. The RBC sensitized with RHP is prepared as follows:
   a. 15 µl of RHP (3 µg) is added to 0.8 ml PBS, pH 6.4.
   b. 0.8 ml of the 3% tanned RBC is mixed with the RHP solution prepared in (a).
   c. Incubate at 37° C. for 15 minutes. Invert tube to mix every 5 minutes.
8. The RBC sensitized with BAF is prepared as follows:
   a. 0.8 ml of PBS, pH 6.4 containing 0.05% BAF is added to 0.8 ml of 3% tanned RBC.
   b. Incubate at 37° C. for 15 minutes. Invert tube to mix every 5 minutes.
9. After the 15 minute incubation, the tubes are centrifuged at 2,000 rpm for 12 minutes. Discard supernate and add to each tube 1.6 ml of PBS pH 7.2 containing 0.05% BAF. Mix and incubate at 37° C. for 15 minutes. Invert tube to mix every 5 minutes.
10. Centrifuge tubes at 2,000 rpm for 12 minutes. Discard supernate. Resuspend RBC in PBS, pH 7.2 containing 0.05% BAF to 1.4 times the original volume. This will make an approximate 2% sensitized RBC suspension. These are the cells used to test for the antibody to RHP.
11. Prepare a 1:10 dilution of the rabbit sera, with PBS pH 7.2 containing 0.05% BAF, and inactivate sera at 56° C. for 30 min.
12. Serially dilute the inactivated sera (25 µl volume). Prepare 2 batches.
13. To one batch of serum dilution add 25 µl RBC sensitized with RHP to each dilution.
14. Add to the other batch of serum dilution, 25 µl of RBC sensitized with BAF to each dilution.
15. Incubate at room temperature for 2 hours.
16. The highest dilution that gives a definitive positive value with the batch incubated with RBC sensitized with RHP is the titer. Definitive positive is indicated by a doughnut shape mat of the RBC.
17. The controls should be all negative, with a dot mat RBC sensitized with BAF.

PREPARATION OF ANTI-RHP TOTAL IMMUNOGLOBULIN FROM RABBIT

1. Twenty-five ml of rabbit anti-RHP serum is precipitated with 25 ml of saturated $(NH_4)_2SO_4$ and incubated overnight at 5° C.
2. Next day, it is centrifuged at $8,000 \times g$ for 3-min and the pellet is washed 3X times with 50% $(NH_4)_2SO_4$ by centrifugation.
3. The final pellet was dissolved in 3.5 ml of saline $-0.1\%$ Na Azide and dialyzed against the same solution.

PREPARATION OF ANTI-RHP IgG FROM RABBIT

1. The solution from Item 3 above is further dialyzed in 10 mM Na phosphate buffer pH 8.0 containing 0.05% Na Azide.
2. The dialyzed globulin solution is then chromatographed on DEAE cellulose column using 30 mM Na-phosphate buffer pH 8.0 containing 0.05% Na Azide.
3. The fractions containing the IgG peak are pooled.
4. The IgG solution is concentrated by precipitating in an equal volume of saturated $(NH_4)_2SO_4$ solution and centrifuged.
5. The pellet is suspended in about 10 ml saline and dialyzed to remove $(NH_4)_2SO_4$.

As is known, IgG can be separated into two different fractions by the action of two different enzymes. The enzyme pepsin produces the $F(ab')_2$ fraction. Papain produces the Fab fraction.

The following procedures may be employed to prepare the separate fractions from the anti-RHP IgG from rabbit.

PREPARATION OF $F(ab')_2$ ANTI-RHP FROM RABBIT IgG

1. IgG solution—175 mg in 5 ml
2. Dialyze in 0.05M acetate buffer pH 4.0 in 0.25% sodium chloride solution.
3. Dissolve 15 mg pepsin in 2 ml of the acetate buffer.
4. Filter the pepsin through a Nalgene filter 0.45 mm.
5. Wash the filter with 2 ml of the acetate buffer. Repeat 3 times.
6. Filter the IgG into the pepsin solution.
7. Incubate overnight at 37° C.
8. Chill and centrifuge at $8,000 \times g$ for 30 minutes.
9. Add $(NH_4)_2SO_4$ crystals to the supernatant to make a 60% solution; containing 5.26g $(NH_4)_2SO_4$ for each 13.5 ml of supernate.
10. Centrifuge at $8,000 \times g$ for 30 minutes.
11. The pellet is dissolved in 2 ml of 0.1M Na phosphate buffer pH 8.0.
12. Dialyze against this buffer overnight at 5° C. with multiple changes.
13. Chromatograph dialyzed $F(ab')_2$ on Biogel 5M (medium mesh).
14. Pool fractions containing the $F(ab')_2$.

PREPARATION OF Fab ANTI-RHP FROM RABBIT IgG

1. IgG solution: 100 mg in 5 ml saline.
2. Dialyze in 0.1M Na acetate buffer pH 5.5: 0.05% Na Azide.
3. To the dialyzed IgG solution add 0.2 ml latex-papain (1819 units/mg, 31.7 mg/ml) suspension in 0.002M EDTA and 0.0005M dithiothreitol.
4. Incubate at 37° C. for 8 hours with occasional shaking to keep the latex in suspension.
5. Centrifuge at $3,000 \times g$ at room temperature for 30 minutes.
6. Dialyze supernate against multiple changes of 0.01M acetate buffer pH 5.5 containing 0.05%; Na Azide.
7. Apply sample to CM-cellulose column.
8. Elute the Fab fraction using 0.05M acetate buffer pH 5.5.
9. Pool the fractions containing the Fab.

RHP can be employed to produce monoclonal antibodies to RHP utilizing the procedure described by Fazekus et al: J. Immunol. Methods 35:1, 1980. The essentials of the procedure are as follows:

1. Immunize an animal, preferably a rodent such as a rat or mouse with RHP.
2. Isolate B-lymphocytes, suitably spleen lymphocytes, from the immunized animal.
3. Fuse the isolated B-lymphocytes with myeloma cells from an animal, preferably a rodent such as a rat or mouse.

4. Select from the fused cells those hybridoma cell lines which react positively with RHP.

5. Clone the hybridoma cells to produce additional monoclonal antibody.

Procedures for performing each of these steps are well known to those skilled in the art who will also know the necessary reagents and how to prepare or obtain them.

To produce a much greater concentration of less pure antibody, the selected hybridoma may be injected into mice, preferably syngenic or semi-syngenic mice. The hybridoma will cause formation of antibody producing tumors in the mice after a suitable incubation time, which will result in high concentration of the desired antibody (about 5-20 mg/ml) in the blood stream and peritoneal exudates (ascites) of the host mouse. Although the host mice also have normal antibodies in their blood and ascites, the concentration of these normal antibodies is only about 5% of the monoclonal antibody concentration. Moreover, since these normal antibodies are not anti-human B-cell in their specificity, the monoclonal antibody obtained from the harvested ascites or from the serum is essentially free of contaminating antibodies.

6. RA DETECTING SECTION

Table 5 shows the positive enhancement of the Clq precipition ring using the S1 fractions obtained from a number of individuals including normals and those afflicted with various arthritides including RA and the other diseases indicated. The numbers in parentheses indicate the number of patients in each group.

The S1 fractions consisted of the proteins eluted from the euglobulin fraction of dialyzed serum by 0.026M EGTA. 5 ul of solution containing 3.75 $\mu$g of S1 protein and 0.85 $\mu$g of purified Clq was added to each well of the agarose gel containing anti-Clq. The purified Clq solution contained 170 $\mu$g/ml as determined by the hydroxyproline method of Rosano et al referred to above. The amount added per well (0.83 $\mu$g) produced a precipitin ring having a diameter of 140 mm in the absence of added protein. The apparent Clq concentrations are RID estimates using Clq-depleted serum to establish the standard curve. The percent enhancement is the average increase calculated from the Clq determined by the hydroxyproline method.

TABLE 5

Effect of S1 fractions on the size of the Clq precipitin ring

| Source of S1 | Apparent Clq concentration | % enhancement |
|---|---|---|
| Normal (19) | 174 ± 2 | 2.4 |
| Gout (15) | 182 ± 6 | 7.2 |
| SLE (5) | 172 ± 1 | 1.1 |
| AS (4) | 183 ± 7 | 6.5 |
| PsA (3) | 178 ± 3 | 3.0 |
| RA (44) | 216 ± 14 | 27.1 |

As will be seen, the increases in the diameter of the rings for RA patients varies from 16% to 73%. The average was 27.1%. The average enhancement with normals and with other arthritides patients is shown in the table. It will be apparent that the RHP in RA patients is unique in its ability significantly to enhance the size of the Clq precipitin ring. One utility of RHP, therefore, is as a diagnostic test for RA patients. Another is for the production of RHP antibodies, both polyclonal and monoclonal.

RHP serum levels can also be employed to monitor the course of RA treatment and to predict the recurrence of the disease. This is apparent from a test in which an RA patient whose disease was in remission for over a year had normal Clq serum levels (68-72 $\mu$g/ml) and no detectable RHP. While still clinically asymptomatic, his Clq serum level increased to 102 $\mu$g/ml and he became RHP positive. A month later, his Clq serum level was 98 $\mu$g/ml, he was still RHP positive, and his disease had become active.

In connection with the previous observation it should be pointed out that (1) the observation of increased RHP alone is sufficient to reach the necessary conclusions, and (2) the observation of increased Clq is not a satisfactory test for RA since the test is too complicated to be performed in the doctors office or in a clinical laboratory which lacks sophisticated equipment, and since it occurs in about 8% of normals, and is rapidly depleted in RA complicated by vasculitis.

One of the most important medical uses for the RHP of this invention is for the production of antibodies to RHP. These, in turn can be employed to detect RHP in currently afflicted individuals, individuals in remission, or individuals at risk of the occurrence of the disease. For these diagnostic purposes the polyvalent or monoclonal antibody will react with the RHP factor from the individual under test to produce, in the case of positive individuals, a detectable product. An antibody composition used in any test designed to determine the presence of RHP must contain sufficient antibody to react with the RHP, which for this purpose may be considered an antigen, to produce a detectable product. Such diagnostically effective amounts of antibody will vary appreciably with a number of factors well known to those skilled in the art. These include, for example, the sensitivity and specifically of the test employed, the instrumentation available and the amount of sample under test.

Any of a large number of clinical tests may be employed utilizing the antibodies of this invention. Typical tests include radio-immunoassay, enzyme linked immunoassay, precipitation, agglutination, direct and indirect immunofluorescence, and complement fixation. These tests may employ competitive and sandwich type assays.

The tests may employ detectable labels. The RHP (antigen), the antibody, or an antiantibody such as goat anti-rabbit serum may be labeled. Useful labels include fluorescent labels such as fluorescein, rhodamine or auramine. Radioisotopes such as $^{14}C$, $^{131}I$, $^{125}I$ and $^{35}S$ may be employed. Enzyme labels which may be utilized include, for example, horse radish peroxidase, $\beta$-D-glucosidase, $\beta$-D-galactosidase, urease, glucose oxidase plus peroxidase, and acid phosphatase. Methods for labeling biological products such as cells, antibodies, antigens and antisera are well known and need not be described.

There are several currently available procedures for detecting these labels including, for example, colorimetric, spectrophotometric, fluorospectrophotometric and gasometric techniques, as well as various instrumental methods of detecting isotopes.

All of the tests which may be usefully employed in accordance with this invention involve the formation of a detectable reaction product which includes an antibody of the invention and the RHP factor. Of course there may be other components such as an anti-antibody in the detectable reaction product.

7. TEST KITS

A wide variety of test kits are possible to take advantage of the advances in the diagnostic arts made possible by this invention. Some will be described here. Others can be devised by those skilled in the art.

The prime reaction in a test kit could be between RHP in the serum and the Fab or F(ab')$_2$. After the immune reaction, the unreacted serum is removed by washing. Whole anti RHP IgG is then used to react with free antigenic sites on the Fab or F(ab')$_2$ RHP. The use of Fab or F(ab')$_2$ as the first antibody obviates the possibility of the binding of RF to the Fc portion of whole IgG.

The descriptions set forth above are directed to the preparation anti-RHP IgG from rabbits and to the preparation of the products of papain and pepsin digests of this material. The following description of test kits and test methods will be based on the rabbit preparation. In fact rabbits are the preferred source of the IgG and its fractions. Those knowlegdable in the field will recognize that the description utilizes the rabbit only as exemplary. Other animals can be employed, and this will require some modification of the other reagents used in the tests and in the kits. Such modifications will be readily apparent to the skilled artisan.

Any of a variety of adsorbents can be used. These include for example glass or plastic surfaces which may be the inner surfaces of test tubes or a surface of a test plate. Typical examples of flat surfaces especially useful in the enzyme linked immunoassay procedure (ELISA) or the radioimmunoassay procedure (RIA) include glass, nitrocellulose paper or plastics such as polystyrene, polycarbonate or various polyvinyls. Particles which can be used for macroscopic procedures wherein the reaction product can be detected visually, e.g. the hemagglutination procedure, include biological particles such as sheep red blood cells or human group O red blood cells, and biologically inert particles such as charcoal, bentonite or latex beads. The latter can be formed of polystyrene, polyvinylpyrrolidone or various polyvinyls.

The ligands can be attached to the surface by direct adsorption, forced adsorption and coupling in accordance with known procedures. In the case of red blood cells, attachment can be accompanied by tanning or pretreatment with chromic chloride.

A typical test kit for use with ELISA or RIA tests will contain:
1. Plate with absorbed Fab, F(ab')$_2$ anti-RHP or both; typically from rabbit anti-RHP IgG.
2. Rabbit anti-RHP whole IgG.
3. Labeled Protein A, or labeled goat or sheep anti-rabbit IgG, Fc fragment.

The kit may also contain appropriate buffers such as PBS containing 1% to 3% BSA at pH 7.2 and appropriate RHP positive and negative controls. These materials may be provided with the kit or may be separately provided or prepared.

The term "plate" is used in the broad sense to include any flat surface such as described above.

In practice such a kit would be employed as follows:
1. Incubate the plate with the serum of the patient under test for an appropriate time and temperature, e.g. from 2 to 4 hours at 37° C.
2. Wash with PBS·BSA.
3. Incubate with untagged rabbit anti-RHP whole IgG and wash with the same buffer.
4. Incubate with Protein A or sheep or goat anti-rabbit IgG, Fc fragment which has been tagged with a detectable label and wash with the same buffer.
5. Detect the formation of a reaction product in the case of a positive test by detecting the label by any of the procedures described above.

Another typical kit for use with ELISA or RIA will contain:
1. A plate with adsorbed Fab, F(ab')$_2$ anti-RHP, or both, typically from rabbit anti-RHP IgG.
2. Labeled rabbit anti-RHP IgG fraction.

This kit also may contain appropriate buffers and positive and negative controls as described above.

The use of this kit will be similar to the use of the first kit except that Steps 3 and 4 are omitted.

A typical kit for use with particulate or macroscopic systems will contain a latex or other particle with adsorbed Fab anti-RHP, typically from rabbit anti-RHP IgG. The kit may also contain appropriate buffers and positive and negative controls.

In practice the particles with the adsorbed antibody fraction will be incubated with the dialyzed serum under test. A positive test can be detected visually.

Other modifications of the particle or macroscopic test kits include:
1: F(ab')$_2$ adsorbed on particles and suspended in a buffer medium containing F(ab')$_2$ in solution.
2: F(ab')$_2$ adsorbed on particles and suspended in a buffer medium.
3: Fab adsorbed on particles and suspended in a buffer medium.
4: Fab adsorbed on particles and suspended in a buffer medium containing F(ab')$_2$ in solution.

Typically the Fab and F(ab')$_2$ will be from rabbit anti-RHP IgG. The kit may also contain positive and negative controls together with PBS·BSA or other suitable buffer.

With each of these kits, the dialyzed serum under test will be incubated on a slide with the kit reagent and, in the case of a positive test, the reaction product will be observed visually.

What is claimed is:
1. A rheumatoid arthritis factor isolated from the sera of human rheumatoid arthritis patients and identifiable by the following characteristics:
(a) isoelectric pH range of 5.1 to 5.3
(b) precipitated from human serum in 0.02 molar acetate buffer at pH 5.51
(c) soluble in 0.026 molar ethylene glycol tetraacetic acid (EGTA) at pH 7.5
(d) present in euglobulin fraction of human sera
(e) molecular weight of about 135,000 as detected by sodium dodecyl sulfate polyacrylamide gel electrophoresis
(f) enlarges the size of the Clq precipitin ring in radial immunodiffusion
(g) inhibits the hemolytic activity of Clq
(h) inhibits the binding of Clq to fibronectin
(i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |

| | |
|---|---|
| Tyrosine | |
| Lysine | |
| Arginine | |

(j) nonreactive with antibodies in human IgG, IgA or IgM.

2. An antibody to a rheumatoid arthritis factor, said factor isolated from the sera of human rheumatoid arthritis patients and identifiable by the following characteristics:
   (a) isoelectric pH range of 5.1 to 5.3
   (b) precipitated from human serum in 0.02 molar acetate buffer at pH 5.51
   (c) soluble in 0.026 molar ethylene glycol tetraacetic acid (EGTA) at pH 7.5
   (d) present in euglobulin fraction of human sera
   (e) molecular weight of about 135,000 as detected by sodium dodecyl sulfate polyacrylamide gel electrophoresis
   (f) enlarges the size of the Clq precipitin ring in radial immunodiffusion
   (g) inhibits the hemolytic activity of Clq
   (h) inhibits the binding of Clq to fibronectin
   (i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |
| Tyrosine | |
| Lysine | |
| Arginine | |

(j) nonreactive with antibodies to human IgG, IgA or IgM.

3. The F(ab')$_2$ fraction of the antibody of claim 2.

4. The Fab fraction of the antibody of claim 2.

5. A composition containing a diagnostically effective amount of the F(ab')$_2$ fraction of an antibody to a rheumatoid arthritis factor, said factor isolated from the sera of human rheumatoid arthritis patients and identifiable by the following characteristics:
   (a) isolectric pH range of 5.1 to 5.3
   (b) precipitated from human serum in 0.02 molar acetate buffer at pH 5.5
   (c) soluble in 0.026 molar ethylene glycol tetraacetic acid (EGTA) at pH 7.5
   (d) present in euglobulin fraction of human sera
   (e) molecular weight of about 135,000 as detected by sodium dodecyl sulfate polyacrylamide gel electrophoresis
   (f) enlarges the size of the Clq precipitin ring in radial immunodiffusion
   (g) inhibits the hemolytic activity of Clq
   (h) inhibits the binding of Clq to fibronectin
   (i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |
| Tyrosine | |
| Lysine | |
| Arginine | |

(j) nonreactive with antibodies to human IgG, IgA or IgM.

6. A composition containing a diagnostically effective amount of the Fab fraction of an antibody to a rheumatoid arthritis factor said factor, isolated from the sera of human rheumatoid arthritis patients and identifiable by the following characteristics:
   (a) isoelectric pH range of 5.1 to 5.3
   (b) precipitated from human serum in 0.02 molar acetate buffer at pH 5.5
   (c) soluble in 0.026 molar ethylene glycol tetraacetic acid (EGAT) at pH 7.5
   (d) present in euglobulin fraction of human sera
   (e) molecular weight of about 135,000 as detected by sodium dodecyl sulfate polyacrylamide gel electrophoresis
   (f) enlarges the size of the Clq precipitin ring in radial immunodiffusion
   (g) inhibits the hemolytic activity of Clq
   (h) inhibits the binding of Clq to fibronectin
   (i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |
| Tyrosine | |
| Lysine | |
| Arginine | |

(j) nonreactive with antibodies to human IgG, IgA or IgM.

7. A method of detecting rheumatoid arthritis in a human which comprises incubating the serum from an individual under test with a composition containing a diagnostically effective amount of the F(ab')$_2$ fraction, the Fab fraction or a mixture of such fractions of an antibody to a fheumatoid arthritis factor, said factor, isolated from the sera of human rheumatoid arthritis patients and identifiable by the following characteristics:
   (a) isoelectric pH range of 5.1 to 5.3
   (b) precipitated from human serum in 0.02 molar acetate buffer at pH 5.5
   (c) soluble in 0.026 molar ethylene glycol tetraacetic acid (EGTA) at pH 7.5
   (d) present in euglobulin fraction of human sera
   (e) molecular weight of about 135,000 as detected by sodium dodecyl sulfate polyacrylamide gel electrophoresis
   (f) enlarges the size of the Clq precipitin ring in radial immunodiffusion
   (g) inhibits the hemolytic activity of Clq
   (h) inhibits the binding of Clq to fibronectin
   (i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |
| Tyrosine | |
| Lysine | |
| Arginine | |

(j) nonreactive with antibodies to human IgG, IgA or IgM.

8. A test kit for detecting a human afflicted with rheumatoid arthritis, said kit containing a diagnostically effective amount of the F(ab')$_2$ fraction, the Fab fraction or a mixture of such fractions of an antibody to a rheumatoid arthritis factor, said factor isolated from the sera of human rheumatoid arthritis patients and identifiable by the following characteristics:

(a) isoelectric pH range of 5.1 to 5.3
(b) precipitated from human serum in 0.02 molar acetate buffer at pH 5.5
(c) soluble in 0.026 molar ethylene glycol tetraacetic acid (EGTA) at pH 7.5
(d) present in euglobulin fraction of human sera
(e) molecular weight of about 135,000 as detected by sodium dodecyl sulfate polyacrylamide gel electrophoresis
(f) enlarges the size of the Clq precipitin ring in radial immunodiffusion
(g) inhibits the hemolytic activity of Clq
(h) inhibits the binding of Clq to fibronectin
(i) over 90% by weight of the total molecular weight is accounted for by the following amino acids:

| | |
|---|---|
| Aspartic acid | Alanine |
| Threonine | Valine |
| Serine | Phenylalanine |
| Glutamic acid | Histidine |
| Proline | Glycine |
| Isoleucine | Cysteine |
| Leucine | |
| Tyrosine | |
| Lysine | |
| Arginine | |

(j) nonreactive with antibodies to human IgG, IgA or IgM.

* * * * *